(12) United States Patent
Llinas (10) Patent No.: US 7,257,439 B2
(45) Date of Patent: Aug. 14, 2007

(54) BRAIN-MACHINE INTERFACE SYSTEMS AND METHODS

(75) Inventor: Rodolfo R. Llinas, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/645,328

(22) Filed: Aug. 21, 2003

(65) Prior Publication Data

US 2004/0133118 A1 Jul. 8, 2004

Related U.S. Application Data

(60) Provisional application No. 60/405,192, filed on Aug. 21, 2002.

(51) Int. Cl.
*A61B 5/04* (2006.01)
*A61B 18/04* (2006.01)

(52) U.S. Cl. ........................................ 600/544; 606/32

(58) Field of Classification Search ............... 600/529, 600/531–538, 506, 547, 544, 545, 372, 373, 600/377, 378; 606/32, 4, 35; 607/45, 46, 607/72, 76, 2, 43
See application file for complete search history.

(56) References Cited

U.S. PATENT DOCUMENTS

| | | | | |
|---|---|---|---|---|
| 3,826,244 A | * | 7/1974 | Salcman et al. ............. | 600/377 |
| 4,341,221 A | * | 7/1982 | Testerman ................... | 600/377 |
| 4,852,573 A | * | 8/1989 | Kennedy ..................... | 600/378 |
| 4,913,160 A | * | 4/1990 | John ........................... | 600/544 |
| 4,959,130 A | * | 9/1990 | Josowicz et al. ............ | 205/210 |
| 5,143,089 A | * | 9/1992 | Alt .............................. | 607/121 |
| 5,201,903 A | * | 4/1993 | Corbett et al. ................ | 29/872 |
| 5,391,147 A | * | 2/1995 | Imran et al. ................. | 604/528 |
| 5,515,848 A | * | 5/1996 | Corbett et al. .............. | 600/377 |
| 5,651,767 A | * | 7/1997 | Schulman et al. ............. | 604/8 |
| 5,779,642 A | * | 7/1998 | Nightengale ................. | 600/461 |
| RE35,880 E | * | 8/1998 | Waldman et al. ........... | 600/374 |
| 5,833,603 A | * | 11/1998 | Kovacs et al. .............. | 600/317 |
| 5,843,093 A | * | 12/1998 | Howard, III ................. | 606/130 |
| 6,128,527 A | * | 10/2000 | Howard et al. ............. | 600/544 |

(Continued)

OTHER PUBLICATIONS

Rodolfo R. Llinas et al., "Brain-Machine Interface Via A Neurovascular Approach", Converging Technologies for Improving Human Performance, Jun. 2002, pp. 244-251.

(Continued)

*Primary Examiner*—Charles A. Marmor, II
*Assistant Examiner*—Navin Natnithithadha
(74) *Attorney, Agent, or Firm*—Darby & Darby (57) ABSTRACT

A system and method for interfacing a brain with a machine. An exemplary embodiment of the present invention employs a vascular approach in which one or more nano-electrodes are deployed in vasculature having a close geometric relationship with proximal innervation. Each nano-electrode is preferably deployed in a blood vessel so that its sensing end is at or near a nerve passing close to or intersecting the blood vessel. The sensing end of each nano-electrode is adapted so as to be carried along in the blood stream so as to position the sensing end at a desired point within the blood vessel. An array of nano-electrodes of varying lengths can be used to monitor multiple nerves or neurons along a blood vessel.

27 Claims, 5 Drawing Sheets

U.S. PATENT DOCUMENTS

| | | | |
|---|---|---|---|
| 6,129,685 A * | 10/2000 | Howard, III | 600/585 |
| 6,208,881 B1 * | 3/2001 | Champeau | 600/374 |
| 6,301,492 B1 * | 10/2001 | Zonenshayn | 600/378 |
| 6,374,140 B1 * | 4/2002 | Rise | 607/45 |
| 6,416,520 B1 * | 7/2002 | Kynast et al. | 606/130 |
| 6,615,067 B2 * | 9/2003 | Hoek et al. | 600/381 |
| 6,622,731 B2 * | 9/2003 | Daniel et al. | 128/898 |
| 6,629,990 B2 * | 10/2003 | Putz et al. | 607/113 |
| 6,673,068 B1 * | 1/2004 | Berube | 606/33 |
| 6,853,075 B2 * | 2/2005 | Auner et al. | 257/737 |
| 2001/0014820 A1 * | 8/2001 | Gielen et al. | 607/116 |
| 2002/0117659 A1 * | 8/2002 | Lieber et al. | 257/14 |

OTHER PUBLICATIONS

Rodolfo R. Llinas et al., "Neuro-vascular central nervous recording/stimulating system: Using nanotechnology probes", Journal of Nanoparticle Research, 2005, vol. 7, pp. 111-127.

* cited by examiner

FIG. 5A binary output

FIG. 5B threshold level

FIG. 6A

Injection Device

Catheter in Aorta

Femoral Artery

BRAIN-MACHINE INTERFACE SYSTEMS AND METHODS

PRIORITY DATA

This application claims priority from U.S. Provisional Application Ser. No. 60/405,192 filed Aug. 21, 2002, which is incorporated herein by reference.

FIELD OF THE INVENTION

The present invention relates to systems and methods for providing an interface between a brain and a machine.

BACKGROUND INFORMATION

When considering the role of neuroscience in modern society, the issue of a brain-machine interface (e.g., between a human brain and a computer) is one of the central problems to be addressed. Indeed, the ability to design and build new information analysis and storage systems that are light enough to be easily carried, has advanced exponentially in the last few years. Ultimately, the brain-machine interface will likely become the major stumbling block to robust and rapid communication with such systems.

To date, developments towards a brain-machine interface have not been as impressive as the progress in miniaturization or computational power expansion. Indeed, the limiting factor with most modern devices relates to the human interface. For instance, buttons must be large enough to manipulate and displays large enough to allow symbol recognition. Clearly, establishing a more direct relationship between the brain and such devices is desirable and will likely become increasingly important.

With conventional means, brain activity can be recorded from the surface of the skull. In the case of electro-encephalography (EEG), electrodes are placed on the skull and record activity occurring on the surface of the brain. In the case of magneto-encephalography (MEG), recording probes are also placed on the surface, but through triangulation brain activity can be mapped in three dimensions.

Such methods as EEG and MEG, while minimally invasive, suffer from poor resolution and distortion due to the deformation of electromagnetic fields caused by the scalp and skull. To overcome these limitations with known technology requires the much more invasive option of opening the skull and inserting electrodes into the brain mass. Similarly, to stimulate the brain as is done therapeutically for some patients with Parkinson's disease or the like, the skull must be opened and electrodes inserted.

As the need for a more direct relationship between the brain and machines becomes increasingly important, a revolution is taking place in the field of nanotechnology (n-technology). Nanotechnology deals with manufactured objects with characteristic dimensions of less than one micrometer. It is the inventors' belief that the brain-machine bottleneck will ultimately be resolved through the application of nanotechnology. The use of nanoscale electrode probes coupled with nanoscale electronics seems promising in this regard.

To date, the finest electrodes have been pulled from glass. These microelectrodes have tips less than a micron in diameter and are filled with a conductive solution. They are typically used for intracellular recordings from nerve and muscle cells. A limitation is that activity is recorded from only one cell at a time. It has been possible, however, to obtain recordings from over 100 individual cells using multi-electrode arrays. Nonetheless, this is an invasive procedure as the electrodes are lowered into the brain from the surface of the skull.

In addition to probing large numbers of points in the brain, the need also exists for processing the large number of signals thus captured and analyzing them in a meaningful way. Methods for processing and displaying signals from multiple sites within the brain have been developed for multi-electrode work with animals and for MEG work with human subjects What is required is a robust and non-invasive way to tap, address and analyze brain activity that is optimized for future brain-machine interaction.

In addition to serving as a means of interacting with machines, a brain-machine interface could also be useful in the diagnosis and treatment of many neurological and psychiatric conditions.

SUMMARY OF THE INVENTION

The present invention relates to a brain-machine interface which is secure, robust and minimally invasive. In accordance with a first aspect of the present invention, a vascular-based brain-machine interface is disclosed.

The fact that the nervous system parenchyma is permeated by a rich vascular bed makes this space a very attractive area for a brain-machine interface. Gas exchange and nutrient delivery to the brain mass occur in the brain across 25,000 meters of capillaries having diameters of approximately 10 microns. Moving towards the heart, the vessels increase rapidly in diameter with a final diameter of over 20 millimeters.

The present invention employs nano-wire technology coupled with nanotechnology electronics to record activity and/or stimulate the brain or spinal cord through the vascular system. The present invention allows the nervous system to be addressed by a large number of isolated nano-probes that are delivered to the brain via the vascular bed through catheter technology used extensively in medicine and particularly in interventional neuroradiology.

In accordance with the present invention, an exemplary embodiment of a recording device comprises a set of nano-wires (n-wires) tethered to electronics in a catheter such that they spread in a "bouquet" arrangement into a particular portion of the brain's vascular system. Such an arrangement can support a very large number of probes (e.g., several million). Each n-wire is used to record the electrical activity of a single neuron, or small group of neurons, without invading the brain parenchyma. An advantage of such an n-electrode array is that its small size does not interfere with blood flow, gas or nutrient exchange and it does not disrupt brain activity.

The techniques of the present invention are also applicable to the diagnosis and treatment of abnormal brain function. Such technology allows constant monitoring and functional imaging as well as direct modulation of brain activity. For instance, an advanced variation of conventional deep brain stimulation can be implemented in accordance with the present invention.

With the present invention, intravascular neuronal recordings can be amplified, processed, and used to control computer interfaces or artificial prostheses. In controlling computational devices, neuronal activity becomes the user input, very much like the manipulation of devices such as keyboards and mice is today. Such input signals could also be used to control the movement of natural limbs that have been separated from their nerve supply through spinal cord or other injury. Thus while direct interface with "intelligent" devices can significantly improve the quality of life for normal individuals, it can also impact disabled individuals, allowing them to be more fully involved in everyday activities.

Obtaining minimally invasive recordings from the brain can also be a useful diagnostic tool in neurology and psychiatry. It provides a functional image of activity deep within the brain that could be localized with precision when combined with MRI. The arrangement of intravascular nano-electrodes in accordance with the present invention can also be used for localized deep brain stimulation without the current need for opening the skull. One advantage of using intravascular nano-electrodes for therapeutic stimulation is that the position of the stimulating electrodes can be easily adjusted. Such adjustment is difficult with the implanted stimulating electrodes used today.

A brain-machine interface based on the nanotechnology/vascular approach of the present invention also has the advantage of being retrievable in that the nano-scale electrodes are small enough so that even with a large number of electrodes, the interface can be removed without violating the integrity of the brain.

DETAILED DESCRIPTION

In an exemplary embodiment, the present invention relates to a neurovascular interface method and system which entails several aspects that will be described below, including: (a) the determination of optimal trans-vessel recording conditions; (b) techniques for introducing and guiding nano-electrodes (n-electrodes) within vessels; (c) techniques for fixing electrodes in position within vessels; (d) the acquisition of data to aid in the design of the n-electrodes; and (e) the determination of the optimal characteristics for recording electrodes, pre-amplifiers and amplifiers, signal processing and other ways of optimizing the recorded signals.

The optimal conditions for obtaining and holding a robust signal recorded across the vascular system and those factors that influence the robustness of the neurovascular approach will be disclosed.

In accordance with a first exemplary embodiment, trans-vascular activity from the enteric nervous system (ENS) is recorded. Functionally, the ENS is similar to a simple brain in that it is capable of intrinsic reflex responses as well as rhythmic activity. Thus a variety of activity can be recorded in the ENS. Anatomically, the ENS and its blood supply are readily accessible. The innervation of the small intestine is particularly favorable. In mammals, the superior mesenteric artery emerges from the midline of the descending aorta at the level of the kidneys. As the artery descends, it branches off into numerous mesenteric branches. These branches form a latticework of anastomotic loops. Straight arteries (arteriae rectae) course off from the loops and enter the small intestine.

A plexus of nerves lies along the length of the superior mesenteric artery. Just below the level of the renal arteries lies the superior mesenteric ganglion. The superior mesenteric plexus sends nerve fibers along the branches of the mesenteric artery. These nerves branch again at the level of the anastomotic loops and arteriae rectae to enter the small intestine along with the blood vessels.

The mesenteric branches of the superior mesenteric artery, vein, and nerve lie between the peritoneal layers of the mesentery. This pair of semitransparent layers of connective tissue helps to maintain the geometric relationship between the blood supply and the innervation of the intestine. If the neurons are stained with a vital dye such as methylene blue, and a tinted Ringer's solution is used for perfusion, the relationship within the ENS between the stimulating and recording electrodes and signal source can be mapped.

Figure 1:
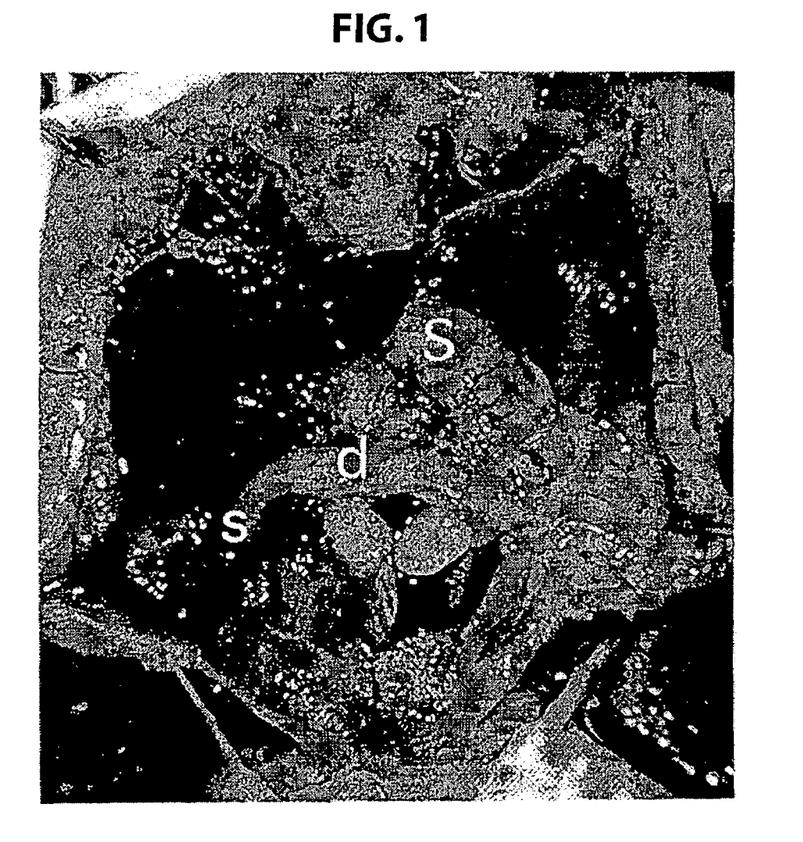
FIG. 1 shows part of the alimentary canal and mesentery of a frog, in situ.

In an exemplary embodiment, the mesentery of a frog is used. This is shown in FIG. 1. There are several advantages of non-mammalian models: 1) they present simpler versions of the human counterpart structures; 2) the tissue is more accessible; and 3) they are less expensive to purchase and maintain than mammalian species. FIG. 1 shows the stomach (S), duodenum (d) and beginning of the small intestine (s) of the frog in situ. A single celiacomesenteric artery branches from the dorsal aorta. The celiac branch of this artery supplies the stomach, whereas the mesenteric branch supplies the duodenum and intestines. The delicate mesentery is visible when the digestive tract is moved from its in situ position.

In accordance with an exemplary embodiment of a method of the present invention, first the brain and upper spinal cord of an anesthetized frog are destroyed by pithing. The mesentery is then lifted from the abdominal cavity through an incision in the abdominal wall. A loop of the intestine is placed on a clear recording chamber and transilluminated. The mesentery is continuously superfused at 3-5 ml/min with frog Ringer solution at 10-12° C. The tissue is viewed with a dissecting microscope. Alternatively, the initial superfusate contains methylene blue (or other vital dye) to locate the innervation of the section of mesentery under study. A sketch is made of the location of the innervation and circulation. A stimulating electrode and a recording (control) electrode are placed on the mesenteric nerve.

Figure 2:
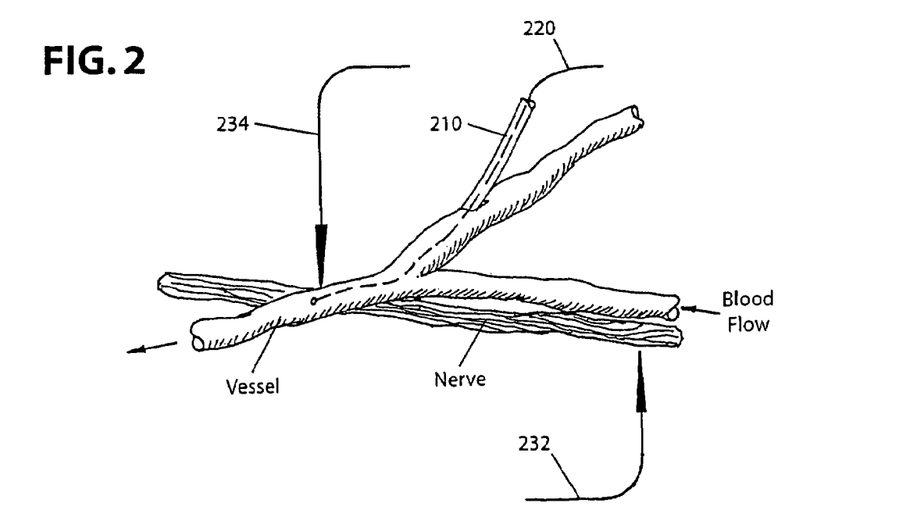
FIG. 2 illustrates the placement of a nano-electrode in vasculature proximate to a nerve fiber whose activity is to be monitored.

FIG. 2 shows a schematic representation of innervation and neighboring vasculature at an exemplary location within the area under study. As shown in FIG. 2, a recording electrode array is introduced near a branch point of a vessel. The vessel is stabilized proximally with a polished glass rod or occluded. A glass microcatheter 210 threaded with one or more n-electrodes 220 is inserted into the vessel using a micromanipulator. Positive pressure is applied to the end of the catheter to prevent the flow of blood into the catheter and to introduce the electrodes into the vessel. The n-electrode 220 is deployed within the vessel so that the sensing end of the electrode is proximate to the point at which a nerve to be monitored is closest to the vessel.

As shown in FIG. 2, an electrode 232 is used to stimulate the nerve and an electrode 234 is used to record action potentials propagating along the nerve. The electrode 232 can be a conventional twisted pair wire electrode and is placed on the nerve. The electrode 234 can be a conventional ball electrode. The recording electrode 234 is placed proximate to the point at which the nerve crosses or passes in close proximity to the vessel.

It is possible to compare the signals from the intravascular n-electrode 220 to the signals obtained by the extravascular recording electrode 234 located directly near the nerve. The results of such comparisons demonstrate that intravascular recordings are comparable to extravascular recordings.

Each electrode array comprises a very large number of insulated nano wires of different length. The diameter of each electrode can be 0.5-10μ. The number of nano-wires having diameters of 0.5μ that can be deployed via a catheter having a diameter of one millimeter is approximately 3 million. The electrodes may be metal (nanowires) or may be carbon tubes (nanotubes). Micron-size electrodes are available from FHC of Bowdoinham, Me.

Each wire within the array ends in a small, bare, cup-like enlargement. This enlargement provides electrical contact with the surrounding fluid and acts as a "sail" to help move the electrode within the vessel. The optimal size and design geometry of the electrode head depend on the forces acting on an electrode in vessels of different diameters. Once the electrodes are in the blood vessel, they are carried by the blood stream until they extend to their full length.

The smallest vascular elements in the frog mesentery, the capillaries, are significantly larger (15-25μ diameter) than nano-electrodes (0.5-10μ). As such, resistance to movement within small arteries and arterioles is minimal. Although blood pressure decreases with distance from the heart, it is still 20 cm $H_2O$ (15 mm Hg) at the level of the capillaries and should provide an adequate pressure head to move the n-electrodes into place.

The flow velocity and pressure strongly depend on the distance from the heart. In large blood vessels, near the heart, the pressure drastically pulsates with each heart beat and blood velocity is maximal. As vessel diameters decrease with increasing distance from the heart, the total area of the vessels sharply increases. The flow becomes laminar and slow. As such, it can be assumed that the blood current through the free vessel branch (see FIG. 2) is relatively constant.

Figure 3A:
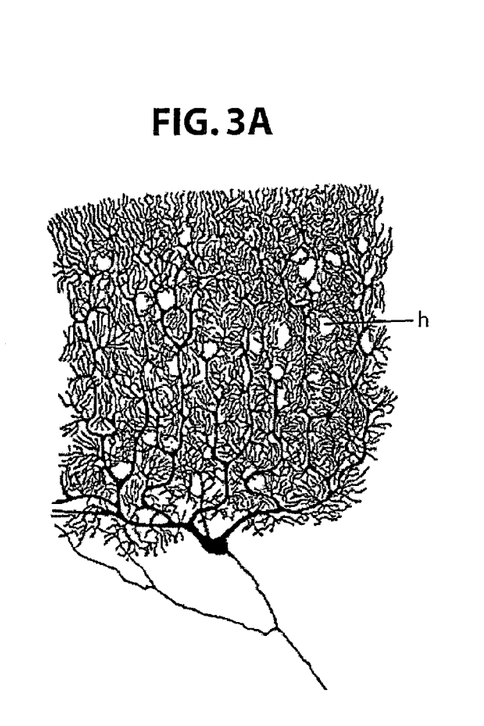
FIGS. 3A and 3B illustrate a Purkinje cell of the brain and its associated vasculature.
Figure 3B:
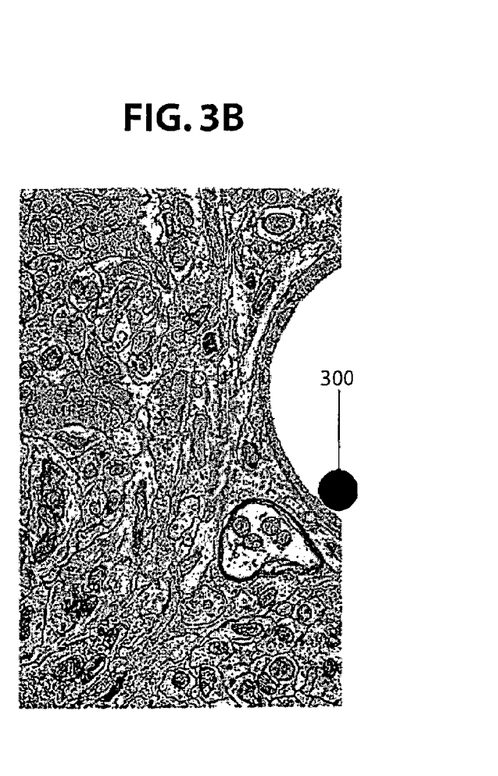

To provide a sense of the size of electrodes involved in the interface of the present invention, FIGS. 3A and 3B illustrate an exemplary neuro-vascular structure in the brain and a nano-wire electrode therein for comparison purposes. FIG. 3A shows an individual Purkinje cell with its characteristic dendritic tree of neurons which is penetrated by multiple capillaries (h) (at least 20 in this case). FIG. 3B shows an enlarged detail view of a portion of FIG. 3A showing a nano-wire 300 having a diameter of 0.9μ within a capillary of the Purkinje cell.

Fluid in the vasculature proximate to innervation tends to be electrically charged since the walls of very small vessels have relatively large openings (i.e., approximately 5% of the cross-sectional area of the vessel) and are penetrable by ions. The blood plasma and extracellular fluid are in ionic and osmotic equilibrium as water and ions move freely between these two compartments through capillary pores. As such, it can be assumed that the electrical potential in a vessel is similar or reflects the electrical potential outside of the vessel. This allows recordation of the activity of a nerve fiber or a neuron located near an n-electrode installed in a nearby vessel.

Larger vessels, however, contain both muscle and fibrous tissue that impede the flow of ions through the vessel walls. (Smooth muscle in large arteries could also generate a low amplitude electrical signal.) Thus, the amplitude of the triggered signal should increase as the electrodes move from arteries to arterioles to capillaries. The key is the amplitude of the electrical field generated by the current source (nerve bundle or plexus in this case). By releasing several n-electrodes of different lengths in a vessel, recordings can be made from several points. Signals from the n-electrodes are then amplified and processed and can be recorded and analyzed. These signals can also be compared to those made using traditional extracellular wire ball electrodes placed near the n-electrodes, as in the arrangement of FIG. 2. Accordingly, data is thus provided on how similar extra- and intra-vessel responses are, and how electrical potential changes along a vessel in space. This helps to determine the maximum distance from a nerve at which signals can be robustly recorded intra-vasculary.

Figure 4:
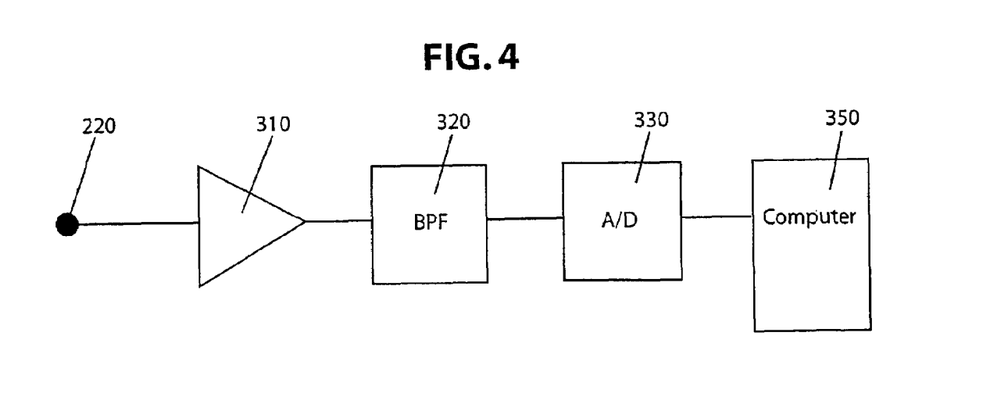
FIG. 4 is a block diagram showing the processing of signals obtained from a nano-electrode.

As shown in FIG. 4, signals from each n-electrode 220 are first amplified, by an amplifier 310, then filtered, by a bandpass filter 320 and then digitized by an analog-to-digital converter (ADC) 330. The data output of the ADC 330 is then provided to a computer 350 for analysis and/or recording. The characteristics of these components will depend on the particular application and considerations such as cost, complexity, size, etc. Performance beyond what is required is costly and usually requires bulky equipment that may thwart the miniaturization and minimal invasiveness of the neuro-vascular approach, particularly where large numbers of electrodes are involved. Listed below are some features that should be considered in choosing the best solution for a particular case.

One consideration is the sampling rate of the ADC 330. The sampling rate must be high enough to properly capture the wave shape being recorded. The mean duration of a spike event is about 4 ms, hence a sampling rate of several thousand Hertz should be acceptable (e.g., 100 kHz or less).

Another consideration is the resolution of the ADC 330. ADCs with resolutions of 4 to 24 bits are available.

Channel crosstalk among multiple n-electrode signal paths is a concern, particularly with increasing numbers of electrodes and decreasing electrode size. There are commercially available analog input modules that are multi-channel. The least expensive type uses a multiplexer feeding a common ADC. For simultaneous sampling, each channel has its own amplifier and sample-and-hold multiplexed into an ADC. For higher speed, each channel may be independent, using a common clock and multi-channel memory. While a single channel may operate well, the performance of such an arrangement while many channels are active simultaneously with high frequency signals can deteriorate drastically. Because the probability of such an event is relatively low, such an arrangement is adequate for most situations. In any case, for good overall performance, the analog circuitry for each individual channel should be isolated from the digital circuitry.

For a slow moving signal in a noisy environment, an integrating ADC may be best. Integrating ADCs are effective in reducing 50/60 Hz noise but have a low conversion rate. The most popular converters are the successive approximation converters. They are available up to 100 MHz, with 12-bit resolution. These converters are available with a pipeline design that is less expensive but introduces delay.

High-speed programmable logic devices, besides providing the ability to synchronously address the module, are also capable of accounting for the pipe line delay. These could be a good choice for large numbers of channels.

Another popular type of converter is the sigma/delta type. A sigma/delta converter uses a single bit ADC and a very high clock speed that is pipelined. Sigma/delta ADCs can have resolutions in excess of 24 bits and are very noise insensitive.

The amplifier signal inputs can be single-ended or differential. The choice depends largely on the type of noise environment in which the system will operate. Differential inputs do provide better common mode noise rejection but generally require more complex and larger circuitry. Because of their small diameters, the resistance of the n-electrodes is significant (e.g., 5-10 MOhms). As such, special care should be given to matching impedances between the electrodes and the signal inputs of the amplifiers 310.

The input amplifier should have a sufficiently wide bandwidth to insure that it can track the signal to be monitored. The sampling clock frequency for the ADC should be at least twice the amplifier bandwidth.

Because the environment in which the system of the present invention operates is generally noisy, input filters 320 are used to improve overall performance. Hardware and/or software filters may be used. The optimal filtering depends on the nature of the noise and its characteristics. In light of the typical frequencies of the signals of neuronal activity, phenomena with frequencies above 100 kHz are generally considered noise and are to be filtered out.

Noise manifests itself as random fluctuations of the local field potential that finally produce some undesirable impact on the signal measured by the electrode. Furthermore, any time that a signal is processed or transferred in any way, noise is introduced. Typically, the noise inherent in the inhomogeneous nature of the environment surrounding an electrode is the most difficult to eliminate.

Noise in the system can be subdivided into two categories: noise inherent to the signal, and noise caused by the external environment. Inherent noise response signals are usually caused by an inhomogeneous and varying environment (e.g., flowing blood), noisy stimulus signals, or some other sources of noise within the test and measurement apparatus itself. External noise is generated outside the test and measurement equipment by sources such as stray electric or magnetic fields, poor shielding or grounding, poor circuit design, noisy power sources, and over-amplification.

Another source of inherent noise is due to the electrode contact potential that exists whenever metallic electrodes interface with a specimen via an electrolyte, as is the case in the environment of the present invention. The random variation of this potential is a source of noise. Statistical analysis of this noise can be used to determine an appropriate compensatory measure.

Unless eliminated, inherent noise will be amplified along with the signal. Hence it is desirable to eliminate it at the initial stages of signal processing. Selective filtering can be employed for this purpose. For example, to eliminate high frequency noise, a frequency window may be created by using band-pass filtering with appropriate cut-off frequencies and roll-offs.

To eliminate so-called common-mode noise (e.g., noise due to power supplies generating electromagnetic waves with a frequency of 50 or 60 Hz) a differential signal may be measured using two electrodes. The differential signal may then be input to a differential amplifier. Common-mode noise can be much stronger than the measured signal. When two inputs are used, a differential amplifier will essentially subtract out the common mode noise present on both inputs and will thus amplify only the true signal.

An important factor that determines a system's tolerance for noise is the amount of noise in the measured signal, i.e., the signal-to-noise ratio (SNR). The SNR is a measure of signal strength relative to background noise. If the incoming signal strength is $V_S$ (usually on the order of millivolts) and the noise level is $V_N$, then the signal-to-noise ratio, in decibels, is:

$$SNR = 20 \log_{10}(V_S/V_N)$$

If $V_S = V_N$, then SNR=0. In this situation, the signal borders on being unintelligible because the noise level severely competes with it. This will cause strong randomness in data and consequently problems in all of the signal processing operations. Ideally, $V_S$ should be much greater than $V_N$ so that the SNR is a large positive number. As an example, for $V_S$=10.0 millivolts and $V_N$=1.0 millivolt, SNR=20 dB, which results in the signal being rather clearly discernable for most applications. If the signal is much weaker but still above the noise, e.g., 2.0 milivolts, then SNR=6 dB, which is a marginal situation. The lower the signal to noise ratio is, the greater the computational effort needed to recover the signal (with some level of errors).

There are several methods of measuring the SNR. In an exemplary method employing an oscilloscope with a bandwidth of 10 MHz, one connects the output from an electrode (after amplification) to be checked and views the "black level" of the signal. The black level should be measured without any external stimulation applied.

TABLE 1

Table 1 gives some guidance for the quality of a measured signal compared to the SNR.

| Signal/Noise Ratio (dB) | Signal/Noise Ratio X:1 | Quality of measured Signal |
|---|---|---|
| 48 | 251 | Excellent |
| 24 | 15.8 | Good |
| 12 | 4 | Poor |
| 6 | 2 | Very poor |

The signals recorded by the n-electrodes represent physical variables (currents or voltages) changing in time with respect to the dynamics of the corresponding nerves. As such, the following factors should be taken into account to optimize the performance of the present invention. First, not all electrodes will be placed at the "right" positions. Some electrodes may be far enough from any neuron so as to be unable to produce reliable data, while others may be damaged. Secondly, two electrodes placed in the vicinity of a single neuron, but at different distances from the neuron will produce different output voltage traces of different amplitudes representing the behavior of the same neuron. Thirdly, the signal to noise ratio may not be optimal if an electrode records the activities of more than one neuron.

Figure 5A:
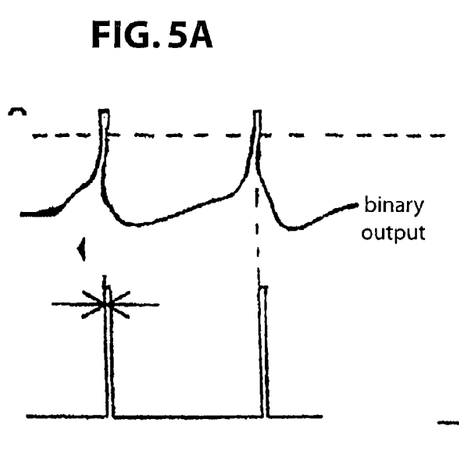
FIGS. 5A and 5B show the neuronal membrane potential as captured and as processed in accordance with the present invention, for a resting and an active state, respectively.
Figure 5B:
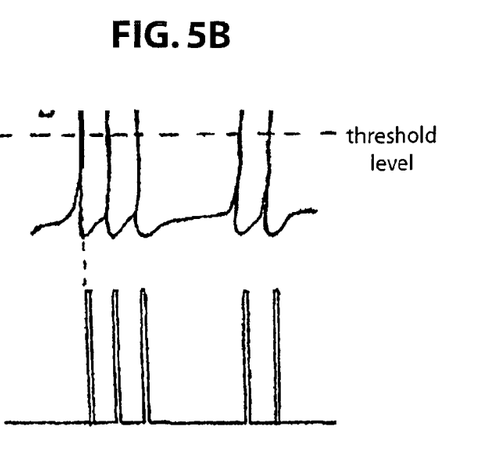

The present invention provides a method of processing the signals captured by the n-electrodes which provides excellent noise performance while also addressing the burdens of dealing with very large numbers of signals. To this end, in an exemplary embodiment of the present invention, the analog output signals of the n-electrodes are converted into binary form as follows:

$$x_n^{bin}(j) = \begin{cases} 1, & \text{if } x_n(t) > x_{thr} \| t - t_{j-1} < \tau \\ 0, & \text{otherwise} \end{cases}$$

where $t_j$ is the time of the beginning of the pulse, $x_n(t)$ is the time signal of electrode n, $\tau$ is the duration of the output pulse (i.e., the digitized signal), and $x_{thr}$ is a threshold level which if exceeded by the input signal $x_n(t)$ will cause the generation of an output pulse. By appropriately choosing the threshold level, $x_{thr}$, the influence of noise is significantly reduced. Furthermore, the problem of dealing with widely varying signal amplitudes is eliminated. The duration $\tau$ of the digitized pulses may be fixed (e.g., 5 ms). The processing represented by the above expression is illustrated in FIGS. 5A and 5B. A hardware implementation of a binary conversion scheme is described more fully below in connection with FIGS. 6B and 6C.

Electrodes which do not exhibit activity beyond a given time period (e.g., 10 sec.) can be ignored. Moreover, the analysis of binary as opposed to analog data provides processing and storage advantages. For example, memory usage is significantly reduced as is computational complexity and time. This is particularly significant in light of the large number of signals to be processed. Furthermore, for purposes of studying action potential dynamics, such a binary representation of neuronal activity should be sufficiently accurate. The different behavioral neuron states produce different firing rates. For example, FIG. 5A shows the typical, "bursting" potential of a neuron at rest, whereas FIG. 5B shows the typical "spiking" potential pattern of an active, "awake" neuron. Because neurons appear to communicate with each other primarily via action potentials, the above simplification is reasonable, without unduly discarding useful signal content.

A rough estimate of input signal bandwidth (informational flow rate), assuming input signals from $10^6$ independent binary variables with a sampling rate of 1 kHz, is $10^6 \times 10^3 = 10^9$ bit/s, or 100 MB per second. Processing for such a flow rate is attainable with present day technologies. Utilization of additional intermediate logic would afford even larger performance increases.

Figure 6A:
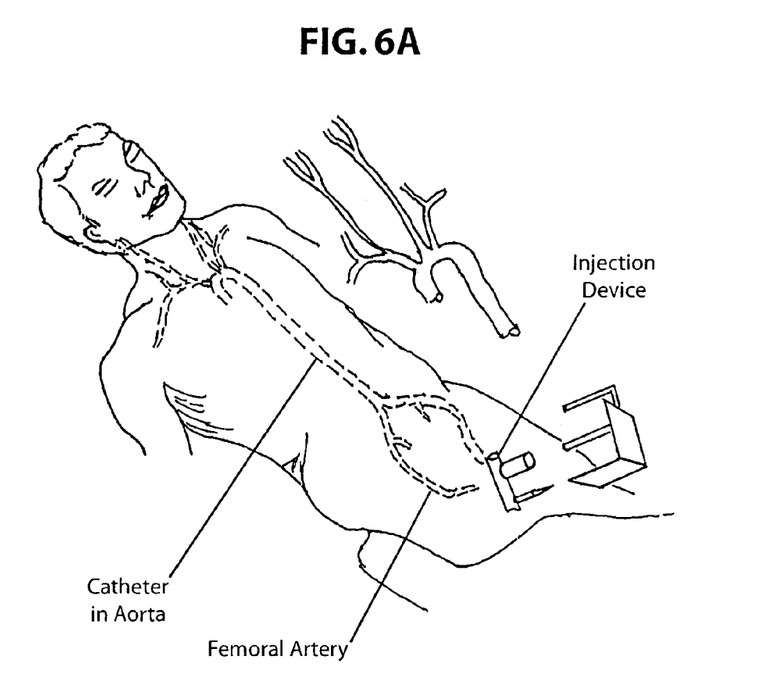
FIGS. 6A through 6C illustrate an exemplary catheter insertion procedure and device in accordance with the present invention.

FIG. 6A illustrates a conventional catheter insertion procedure that can be used to deploy an interface device in accordance with the present invention. As shown in FIG. 6A, a catheter is introduced into the femoral artery and is pushed up to a vascular territory to be addressed. The catheter may also be inserted into the carotid or the sub-clavial artery. Such a procedure is similar to interventional neuro-radiology techniques where catheters are guided to any portion of the central nervous system.

Once an area to be monitored or stimulated is reached, a set of leads held inside the catheter head are allowed to extend and become randomly distributed into the brain's circulatory system. Since a catheter can be placed in any major brain vessel, the maximum length of the nano-wire electrodes required to reach any capillary bed is on the order of 2 to 3 cm. Hence a large number of electrodes can cover any region of the central nervous system from the parent vessels harboring the stem catheters.

Figure 6B:
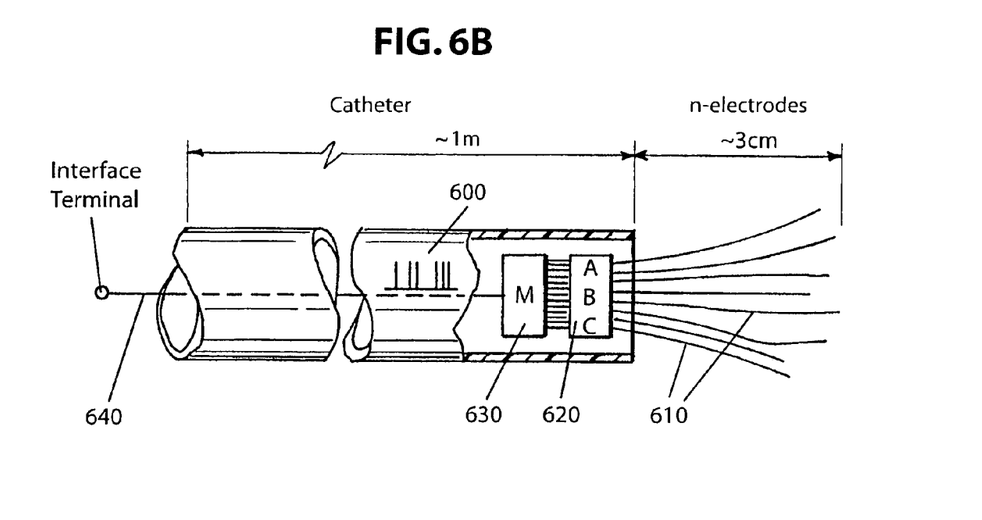

FIG. 6B is a schematic representation of an exemplary embodiment of a catheter 600 of a brain-machine interface device in accordance with the present invention. A plurality of single n-wire electrodes 610 are coupled to an amplifier/binary converter (ABC) 620 which is in turn coupled to a multiplexer (M) 630. As shown in greater detail in FIG. 6C, the ABC 620 can be implemented with an amplifier 612.1-612.N and a Schmitt trigger 615.1-615.N for each of the N nano-wire electrodes 610.1-610.N. Each Schmitt trigger transforms the action potential from the respective amplifier into a pulse train having a binary value (HIGH/LOW or 0/1). As such, at any given instant, only one bit is required to represent the action potential on each nano-wire electrode.

The outputs of the multiple Schmitt triggers are multiplexed by the multiplexer 630 onto a micro wire 640 and provided to a terminal interface for coupling to a computer or the like (not shown). In an exemplary embodiment, each electrode 610 has a diameter of approximately 0.5μ and a length of 3 cm or less and the micro-wire 640 is approximately one meter long. A single catheter may carry one or more arrangements such as those shown in FIGS. 6B and 6C.

Figure 6C:
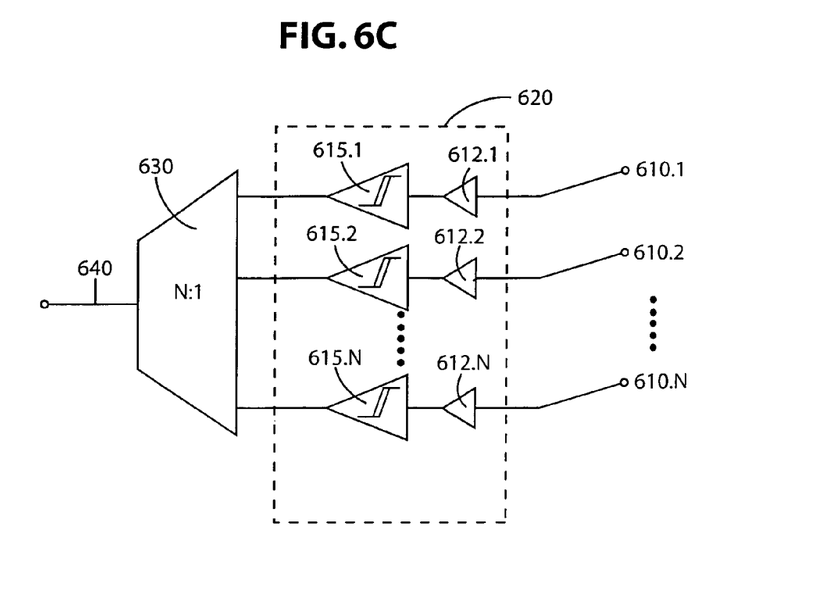

Thus, as described above, the ABC 620 amplifies and digitizes the signals on the nano-wire electrodes 610. The multiple digital outputs of the ABC 620 are multiplexed by the multiplexer 630 into a single stream of serial data which is conveyed by the micro-wire 640 to a computer for processing. In this way, a small number of inexpensive and robust micro-wires can be used along the catheter length to convey data from a much larger number of nano-wire electrodes.

The nano-wires 610 are preferably of different lengths so as to cover multiple points along the vessels in which they are deployed. The circuitry 620, 630 is preferably located in or proximate to the tip of the catheter 600 so as to minimize the length of the nano-wires and to thus optimize noise performance. The circuitry 620 and 630 is also preferably implemented with integrated circuit technology in order to fit in the limited space available in or proximate to the tip of the catheter 600. Prior to deployment, the nano-wires 610 are coiled-up within a compartment at the tip of the catheter. As the compartment is open (e.g., mechanically like a trap door) the electrodes deploy and extend along the vessels, carried by the blood flow and branching out along the branching vessels.

In addition to the hardware-related aspects described above, the present invention also provides the software methods for reading, storing and contextualizing the enormous amount of neuronal information that is provided by the above-described vascular apparatus. Such processing helps provide an understanding of neuronal activity, thereby providing a significant window into brain function, further defining the relations between electrophysiology and the cognitive/motor properties of the brain. The methods of the present invention include signal processing capable of classifying brain states based on neuronal unit activity and field potential analysis. The present invention also provides a package of algorithms and a computational toolkit that is appropriate and effective for data analysis and decision making.

The present invention provides software methods for classifying brain states based on neuronal unit activity and field potential analysis. A goal of such methods is to correlate, in real time, the moment-to-moment electrical activity of neurons with large functional brain states. It is assumed that the electrical properties of neurons define all possible brain states and that such states co-vary systematically with the global state dynamics. However, this does not imply that there exists one-to-one correspondence between purely local patterns of brain activity and a particular set of functional states. Physically, the generation of a new functional state in the brain, for instance the transition "sleep-wakefulness,"

corresponds to activity reorganization in many groups of neurons. There are practically an infinite number of possible patterns, each slightly different from the other. The approach is to map the small variance patterns into relatively small sets of different functional states. For example, in the simplest case only three global functional states may be considered: 1) sleep, 2) wakefulness, and 3) "none of the above" or uncertain state, e.g., drowsy. The last state is required in order to close the output domain of a mathematical algorithm, since otherwise it would not be possible to solve correctly for any possible input pattern, including the unavoidable impact of noise. Moreover, the third state is vital from a conceptual viewpoint as for instance, to see or not to see light is possible in the awake state only and, hence, during sleep this state could be uncertain.

As mentioned above, an exemplary embodiment of a computational algorithm in accordance with the present invention detects alterations in brain activity that relate to a global change of states. This activity is represented by the set of binary time series taken from many neurons, i.e., by spatiotemporal patterns. The problem is then one of pattern classification, as discussed below. For an algorithm to be useful it must be optimized to: 1) determine the minimal number of hypotheses (possible functional states) concerning the data set; 2) economize on data storage and subsequent data manipulation/calculation; 3) scale for increasing data sets and for the number of functional states; and 4) be robust. In an exemplary embodiment, the present invention provides a method based on a cluster analysis approach.

In the first step, a data set comprising all action potentials over a given time interval is split into J short time intervals by shifting a time window of length T. The time scale T can be varied for different purposes and its choice is a compromise between speed and reliability in data analysis. Each window will be referred to as "an object" or entity assuming that a window encompasses an unchanged functional state. Assuming a correct set of hypotheses concerning the number of clusters, K, (e.g., for three global functional states K=3: wakefulness, sleep, and uncertain state), the J different objects must be related to K functional states.

Figure 7:
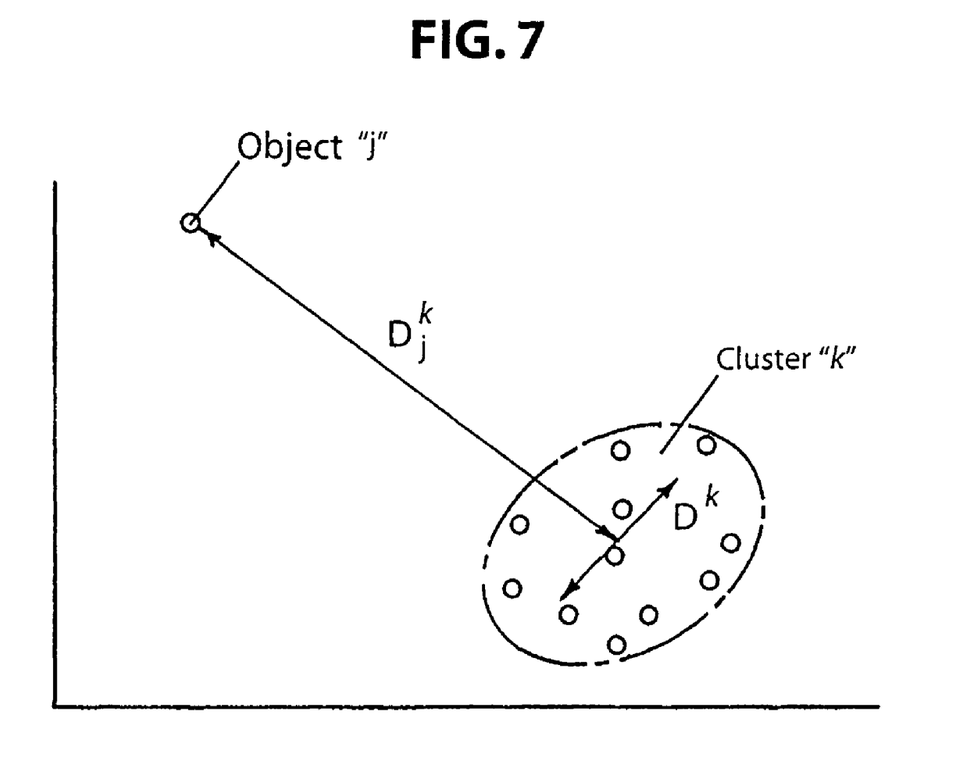
FIG. 7 illustrates the dissimilarity of an object j to a cluster k and the mean dissimilarity within the cluster k.

The algorithm starts with K random clusters, and then moves objects between those clusters in order to assign objects to clusters such that the variance within each cluster would be minimal, while the variance between clusters would be maximal. To implement this function, a measure of dissimilarity between objects is obtained. This can be determined by calculating Euclidean distances between objects in a multi-dimensional space. The average dissimilarity of object j to cluster k (i.e., the distance between j and k) and the average dissimilarity within cluster k are shown in FIG. 7. This algorithm works well under the assumption that the correct dissimilarity has been measured. For time series objects, in the simplest case, neuronal firing rates can be used as coordinates in a multi-dimensional space. Other possible measures, which may be useful in classifying fine functional states such as cognition, includes a dissimilarity matrix based on cross-correlation sums.

The classification algorithm may be referred to as "unsupervised." It is based on the hypothesis of a "good" dissimilarity measure and does not include any optimization. This approach can be upgraded to a supervised training data set, where the correct results of classification are known a priori for a portion of the data and may be used as a feedback reference for improvement of computational speed and reliability. Even after tuning, however, the algorithm may fail because brain plasticity may occur. Thus the possibility of sudden mistakes may be corrected by means of the feedback.

One problem to be solved is the non-stationary nature of brain function. This seems at first glance to be a big obstacle for any analysis. However, a detailed study of the problem indicates that all functional states are temporal and have essentially different time scales. For example, being awake can last for hours, while cognition can be as short as tens of milliseconds. Furthermore, it is possible to assume that only a limited number of functional states can coexist. These two considerations allow building a new adaptive algorithm capable of discriminating, in principle, any possible functional states.

There are three main parameters at play: 1) the length of the time window, T; 2) the number of clusters of objects, K, being separated; and 3) the dissimilarity measurement. The process of classification can be started with relatively long T, and small K. Thus fast processes (functional states) would be eliminated due to averaging over a protracted time. Moreover, functional states with intermediate time scale and with a strong influence on others would be left out due to very rough classification, since the patterns have been split into a small number of clusters. Then, when a first approximation of cluster boundaries is determined and it can reliably detect functional states of the top level, a step down can be taken by decreasing window size T, and by including finer functional states (increasing K). Moreover, it is possible to work "within" a functional state of the upper level and reject all non-fitting objects. Such a modification of the algorithm allows scalability and a method of exploration of all possible functional states. It should be noted that the deeper the process progresses into the functional state hierarchy, the heavier the computation needed. However, the main parts of the algorithm can be easily paralleled and hence effectively performed by parallel computers or other known processors.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are to some degree approximate, and are provided for purposes of description.

What is claimed is:

1. A method of sensing the activity of neural tissue, the method comprising the steps of:
    placing an electrode in a blood vessel proximate to the neural tissue, said electrode being smaller than 10 μm in diameter; and
    monitoring a signal on the electrode by way of a wire connected to the electrode,
    wherein the signal is indicative of the electrical brain activity of the neural tissue.

2. The method of claim 1, wherein the electrode comprises a sensing end, the sensing end of the electrode being placed in the blood vessel proximate to the neural tissue.

3. The method of claim 1, wherein the electrode is inserted into the blood vessel at a point upstream of a junction with another blood vessel.

4. The method of claim 3, wherein a sensing end of the electrode is deployed to a point downstream of the junction.

5. The method of claim 1, comprising the steps of:
placing a further electrode on the neural tissue proximate to the electrode;
applying a stimulus to the neural tissue;
monitoring a further signal on the further electrode after applying the stimulus to the neural tissue; and
comparing the signal to the further signal.

6. The method of claim 1, wherein the electrode comprises a nano-electrode.

7. The method of claim 1, wherein the electrode comprises an array of nano-electrodes.

8. The method of claim 7, wherein the nano-electrodes have different lengths.

9. The method of claim 6, wherein the nano-electrode comprises a cup-like end.

10. The method of claim 1 further comprising the step of stimulating neural tissue by providing a stimulation signal to said electrode.

11. The method of claim 1 further comprising the steps of:
placing a second electrode in a second blood vessel proximate to the neural tissue, said second electrode being of sufficiently small size such that it is capable of being inserted into a capillary; and
providing a stimulation signal to said second electrode.

12. The method of claim 1 further comprising the step of filtering the signal from said electrode.

13. The method of claim 1 further comprising the step of utilizing a differential signal as said electrode signal.

14. The method of claim 1 further comprising the step of classifying brain states based on one of neuronal unit activity and field potential analysis.

15. The method of claim 1 further comprising the step of correlating electrical activity of neurons with brain states.

16. The method of claim 15 further comprising the step of performing pattern classification to determine brain states.

17. A method of sensing the activity of neural tissue, the method comprising the steps of:
inserting an electrode in a blood vessel at a point upstream of a junction with another blood vessel to position the electrode proximate to the neural tissue, said electrode being smaller than 10 µm in diameter; and
monitoring a signal on the electrode by way of a wire connected to the electrode,
wherein the signal is indicative of the electrical brain activity of the neural tissue.

18. A method of stimulating neural tissue, the method comprising the steps of:
placing an electrode in a blood vessel proximate to the neural tissue, said electrode being smaller than 10 µm in diameter; and
providing a signal on the electrode by way of a wire connected to the electrode,
wherein the signal stimulates the electrical brain activity of the neural tissue.

19. The method of claim 18, wherein the electrode comprises an end, the end of the electrode being placed in the blood vessel proximate to the neural tissue.

20. The method of claim 18, wherein the electrode is inserted into the blood vessel at a point upstream of a junction with another blood vessel.

21. The method of claim 20, wherein an end of the electrode is deployed to a point downstream of the junction.

22. The method of claim 18, wherein the electrode comprises a nano-electrode.

23. The method of claim 18, wherein the electrode comprises an array of nano-electrodes.

24. The method of claim 23, wherein the nano-electrodes have different lengths.

25. The method of claim 22, wherein the nano-electrode comprises a cup-like end.

26. The method of claim 18 further comprising the step of monitoring a monitor signal on said electrode.

27. The method of claim 18 further comprising the steps of:
placing a second electrode in a second blood vessel proximate to the neural tissue, said second electrode being of sufficiently small size such that it is capable of being inserted into a capillary; and
providing a monitor signal to said second electrode.

* * * * *